US006506576B2

(12) United States Patent
Belcher

(10) Patent No.: US 6,506,576 B2
(45) Date of Patent: Jan. 14, 2003

(54) SERUM-AND STEROID-FREE CULTURE MEDIA FOR CEREBELLAR GRANULE NEURONS

(76) Inventor: Scott M. Belcher, 5824 Lee Ave., Little Rock, AR (US) 72205

( * ) Notice: Subject to any disclaimer, the term of this patent is extended or adjusted under 35 U.S.C. 154(b) by 0 days.

(21) Appl. No.: 09/928,214

(22) Filed: Aug. 9, 2001

(65) Prior Publication Data

US 2002/0132345 A1 Sep. 19, 2002

Related U.S. Application Data

(60) Provisional application No. 60/275,767, filed on Mar. 14, 2001.

(51) Int. Cl.$^7$ .................................................. C12Q 1/02
(52) U.S. Cl. ..................... 435/29; 435/379; 435/406; 435/407; 435/402
(58) Field of Search .................... 435/29, 379, 406, 435/407, 402

(56) References Cited

U.S. PATENT DOCUMENTS

| | | |
|---|---|---|
| 5,063,157 A | 11/1991 | Stockinger |
| 5,316,938 A | 5/1994 | Keen et al. |
| 5,326,699 A | 7/1994 | Torishima et al. |
| 5,328,844 A | 7/1994 | Moore |
| 5,405,722 A | 4/1995 | Ponting |
| 5,411,883 A * | 5/1995 | Boss et al. ............... 435/240.2 |
| 5,512,477 A | 4/1996 | Goodrick et al. |
| 5,573,937 A | 11/1996 | Shinmoto et al. |
| 5,641,647 A | 6/1997 | Fischer et al. |
| 5,691,202 A | 11/1997 | Wan et al. |
| 5,712,163 A | 1/1998 | Parenteau et al. |
| 5,766,948 A | 6/1998 | Gage et al. |
| 5,780,301 A | 7/1998 | Saito et al. |
| 5,908,782 A | 6/1999 | Marshak et al. |
| 5,908,783 A | 6/1999 | Brewer |
| 6,020,197 A | 2/2000 | Gage et al. |
| 6,040,180 A | 3/2000 | Johe |
| 6,043,092 A | 3/2000 | Block |
| 6,048,728 A | 4/2000 | Inlow et al. |
| 6,013,530 A | 8/2000 | Carpenter |
| 6,180,404 B1 | 1/2001 | Brewer |
| 2002/0028510 A1 * | 3/2002 | Sanberg et al. ............. 435/368 |

OTHER PUBLICATIONS

Ahmed, Z ET AL., "Properties of nuerons from dissociated fetal rat brain in serum–free culture," J Neurosci, p. 2448–2462, (1983).
Bhave ET AL., "Brain–derived neurotrophic factor mediates the anti–apoptotic effect of NMDA in cerebellar granule neurons: signal transduction cascades and site of ethanol action," J Neurosci, p. 3277–3286, (1999).
Bottenstein, JE and Sato, GH, "Growth of a rat nueroblastoma cell in serum–free supplemented medium," Proc Natl Acad Sci USA, p. 514–517, (1979).
Bottenstein ET AL., "Selective survival of neurons from chick embryo sensory ganglionic dissociates utilizing serum–free supplemented medium," Exp Cell Res, p. 183–190, (1980).
Brewer, GJ, "Serum–free B27/neurobasal medium supports differentiated growth of neurons from the striatum, substantia nigra, septum, cerebral cortex, cerebellum, and dentate gyrus," J Neurosci Res, p. 674–683, (1995).
Brewer GJ and Cotman CW, "Survival and growth of hippocampal neurons in defined medium at low density: advantages of a sandwich culture technique or low oxygen," Brain Res, p. 65–74, (1989).
Brewer ET AL., "Optimized survival of hippocampal neurons in B27–supplemented Neurobasal, a new serum–free medium combination," J Neurosci Res, p. 567–576, (1993).
Burgoyne ET AL., "Neurotrophic effects of NMDA receptor activation on developing cerebellar granule cells," J Neurocytol, p. 689–695, (1993).
Carroll ET AL., "Investigation of non–NMDA receptor–induced toxicity in serum–free antioxidant–rich primary cultures of murine cerebellar granule cells, " Neurochem Int, p.23–28, (1998).
Choi, DW and Koh, JY, "Zinc and brain injury," Annu Rev Neurosci, p. 347–375, (1998).
Cory ET AL., "Use of an aqueous soluble tetrazolium/formazan assay for cell growth assays in culture," Cancer Commun, p. 207–212 (1991).

(List continued on next page.)

Primary Examiner—James Ketter
(74) Attorney, Agent, or Firm—Christine J. Daugherty

(57) ABSTRACT

The invention is a system for maintenance and high-throughput analysis of cerebellar granule neurons in tissue culture plates under chemically defined conditions. The invention includes serum-free granule culture medium, which is composed of high glucose Dulbecco's Modified Eagle Media (DMEM), NaHCO3, sodium pyruvate, and HEPES, which is subsequently adjusted to pH 7.2. The HEPES buffered DMEM is then supplemented with L-glutamine, KCl, bovine albumin, insulin, transferrin, selenium, penicillin, and streptomycin. Unlike proprietary neuronal culture media, this invention does not include any serum, steroid hormones, phenol red, or added anti-oxidants. The serum-free granule culture medium is then placed in conventional poly-lysine coated tissue culture plates in order to conduct subsequent assays. The invention also includes the ability to package the complete neuronal culture system into a "kit" for isolation, maintenance, treatment, and analysis of cerebellar neurons. A kit would include all the necessary culture medium preparations, tissue culture plates with an appropriate cellular attachment matrix, reagents, disposables and protocols. The kit could be used to evaluate neuronal viability, growth, the role of steroid hormones on neuronal function, drug or toxicant-induced changes in gene expression, or other bioassays. In addition, the invention will be useful in the field of pharmocogenomics because of the ability to analyze small sample sizes.

56 Claims, 15 Drawing Sheets

OTHER PUBLICATIONS

Carrol ET AL., "Investigations of non–NMDA receptor–induced toxicity in serum–free antioxidant–rich primary cultures of murine cerebellar granule cells," Neurochem Int, p 23–28, (1998).

Cull–Candy ET AL., "Noise and single channels activated by excitatory amino acids in rat cerebellar granule neurons," J Physiol (Lond), p. 189–222, (1988).

Cullingford ET AL., "Hormonal regulation of the mRNA encoding the ketogenic enzyme mitochondrial 3–hydroxy–3–methylglutaryl–CoA synthase in neonatal primary cultures of cortical astrocytes and meningeal fibroblasts," J Neurochem, p. 1804–1812, (1988).

Gu ET AL., "Rapid action of 17 beta–estradiol on kainate–induced currents in hippocampal neurons lacking intracellular estrogen receptors," Encorinology, p. 660–666, (1999).

Gu, q and Moss, RL, "17 beta–Estradiol potentiates kainate–induced currents via activation of the cAMP cascade," J Neurosci, p. 3620–3629, (1996).

Hansen ET AL., "Re–examination and further development of a precise and rapid dye method for measuring cell growth/cell kill," J Immunol Methods, p. 203–210, (1989).

Lim, DK And Ho, IK, "Responses to N–methyl–D–aspartate and kainic acid in cerebellar granule cells of lead–exposed rat pups," Neurotoxicity, p. 49–55, (1998).

Liu ET AL., "Mechanism of cellular 3–(4, 5–dimethylthaizol–2–yl)–2,5,–diphenyltetrazolium bromide (MTT) reduction," J Neurochem, p. 581–593, (1997).

Liu ET AL., "Cytotoxic amyloid peptides inhibit cellular 3–(4,5–dimethylthiazol–2–yl)–2,5–diphenyltetrazolium bromide (MTT) reduction by enhancing MTT formazan exocytosis," J Neurochem, p. 2285–2293, (1997).

Mosmann, T, "Rapid colorimetric assay for cellular growth and survival: application to proliferation and cytotoxicity assays," J Immunol Methods, p. 55–63, (1983).

Pemberton ET AL., "High–affinity kainate–type ion channels in rat cerebellar granule cells," J Physiol (Lond), p. 401–420, (1998).

Singer ET AL., "The mitogen–activated protein kinase mediates estrogen neuroprotection after glutamate toxicity in primary cortical neurons," J Neurosci, p. 2455–2463, (1999).

Singh ET AL., "Estrogen–induced activation of mitogen–activated protein kinase in verebral cortical explants: Converegence of estrogen and neurotrophin signaling pathways," J Neurosci, p. 1179–1188, (1999).

Smith, SS, "Estrogen administration increases neuronal responses to excitatory amino acids as a long–term effect," Brain Res, p. 354–357, (1989).

Smith, SS, "Progesterone enhances inhibitory responses of cerebellar Purkinje cells mediated by GABAA receptor subtype," Brain Res Bull, p. 317–322, (1989).

Smith, SS, "Progesterone adminstration attenuates excitatory amino acid responses of cerebellar Purkinje cells," Nueroscience , p. 309–320, (1991).

Toran–Allerand ET AL., "Novel mechanisms of estrogen action in the brain: new players in an old story," Front Neuroendocrinol, p. 97–121, (1999).

Wong et al. "Simplified serum– and steroid–free culture conditions for high–throughput viability analysis of primary cultures of cerebellar granule neurons," Journal of Neuroscience Methods, in press.

Wong, JJ And Belcher, SM, "Serum–and steriod–free primary culture conditions for the maintenance high–throughput viability analysis of cerebellar granule cells," Society of Toxicology, 40th Annual Meeting, Society of Toxicology (San Francisco, U.S.) (Mar. 28, 2001).

* cited by examiner

SERUM- AND STEROID-FREE CULTURE MEDIA FOR CEREBELLAR GRANULE NEURONS

CROSS-REFERENCE TO RELATED APPLICATIONS

The present application claims the benefit of U.S. provisional patent application No. 60/275,767, filed Mar. 14, 2001, which is incorporated herein by reference.

STATEMENT REGARDING FEDERALLY SPONSORED RESEARCH OR DEVELOPMENT

This invention was made with Government support under the terms of Grant No. NS37795 awarded by NIH/NINDS. The Government has certain rights in the invention.

BACKGROUND OF THE INVENTION

1. Field of the Invention

The present invention relates to neuronal culture media that may be used for high-throughput analyses.

2. Brief Description of the Related Art

The ability to maintain isolated neurons in primary culture has been critical in advancing our understanding of the functional basis of the nervous system. In primary neuronal culture studies, the use of defined culture conditions is essential for controlling the concentration of components, such as hormones and growth factors, which may affect the growth and development of cultured neurons.

Primary cultures of cerebellar neurons are an important in vitro model system that has been used because of their small size, the ease with which large numbers of cells can be isolated, and the resulting physical properties. Neonatal rat or mouse cerebellar granule cells are convenient and frequently used in studies with aims ranging from the identification of factors involved in neurogenesis, development, and migration to defining mechanisms of neurotoxicity and cell death (Cull-Candy, et al., *J Physiol,* 400: 189–222, 1988; Pemberton, et al. *J Physiol,* 510: 401–420, 1998; Bhave et al., *J Neurosci,* 19: 3277–3286, 1999). Because cultured granule cells express both $Ca^{++}$ permeable-NMDA and non-NMDA glutamate receptors, these neurons are also an important model used for the analysis of neuronal excitotoxicity (Carroll et al., *Neurochem Int,* 33: 23–28, 1998; Lim and Ho, *J Neurochem,* 69: 581–593, 1998).

Over the past three decades, significant progress has been made in developing conditions for maintaining dissociated neurons in culture without the need for serum supplements. Media supplements, such as the relatively simple N2 medium supplement (Boftenstein and Sato, *Proc Natl Acad Sci U.S.A.* 76: 514–517, 1979) and the more complex neurobasal medium and B27 supplement (NB-B27) were originally designed for optimal viability of neurons in low-density primary culture systems (Brewer and Cotman, *Brain Res,* 494: 65–74, 1989; Brewer et al., *J Neurosci Res,* 35: 567–576, 1993; and Brewer, *J Neurosci Res,* 42: 674–683, 1995).

However, both the N2 and B27 supplements contain significant concentrations of the steroid hormone progesterone and B27 contains unspecified amounts of steroids, non-steroidal hormones, antioxidants, and other factors that may influence the outcome of neurotoxicity studies (Brewer, *J Neurosci Res,* 35: 567–576, 1995). It is well established that the activities of steroidal hormones can affect growth and proliferation mechanisms of cultured neurons (Singh et al., *J Neurosci,* 19: 1179–1188, 1999; Singh et al., *J Neurosci,* 19: 2455–2463, 1999; Toran-Allerand et al., *Front Neuroendocrinol,* 20: 97–121, 1999) as well as influence the functional properties of some neurotransmitter receptors (Smith, *Brain Res,* 503: 354–357, 1989; Smith, *Brain Res Bull,* 23: 317–322, 1989; Smith, *Neurosci,* 42: 309–320, 1991; Gu and Moss, *J Neurosci,* 16: 3620–3629, 1996; Gu et al., *Endocrinology,* 140: 660–666, 1999).

While Carroll et al., *Neurochem Int,* 33: 23–28 (1998), used NB-B27 in neurotoxicity studies of granule cells, the high concentrations of antioxidants contained in this complex media formulation may have masked the effects of many toxicants including excitotoxins and reactive oxygen species. U.S. Pat. Nos. 5,766,948 and 6,020,197 to Gage et al., which are incorporated herein by reference, disclose a medium that can be used both in neuroblast and cellular compositions. However, this medium is supplemented with trophic factors, a component specifically avoided in this invention.

Other studies such as those found in U.S. Pat. No. 6,040,180 to Johe, which is incorporated herein by reference, disclose using a serum-free medium supplemented with numerous growth factors. This culture media described in Johe, is used for generating differentiated neurons, but does not describe a media that can be used for toxicological studies.

Another component found in many types of growth media is phenol red. Phenol red, which is used primarily as a pH indicator, is very commonly used in tissue culture media, but can interfere with many assays. For example, U.S. Pat. No. 5,573,937 to Shinmoto et al., and U.S. Pat. No. 5,316,938 to Keen et al., which are incorporated herein by reference, both disclose media in which one of the components is phenol red.

Factors such as corticosterone, progesterone, retinyl acetate, T3 (triiodo-1-thyronine), α-tocopherol (vitamin E) and phenol red which are present in NB-B27, may influence the outcome of studies assessing the effects of steroids on neuronal growth and development. U.S. Pat. No. 6,103,530 to Carpenter, which is incorporated herein by reference, discloses a culture medium for proliferating mammalian neural stem cells containing neural stem cell growth factors, such as transforming growth factor alpha, epidermal growth factor, or basic fibroblast growth factor. Likewise, U.S. Pat. No. 5,780,301 to Saito et al., also incorporated herein by reference, discloses a serum-free medium for culturing postnatal central neurons but includes the additional components of platelet-derived growth factors, vitronectin, and interleukin-1β, all which may affect neuronal studies.

Studies used to measure neurotoxicity can be affected by added antioxidants in the growth media. Because antioxidants have been shown to efficiently reduce MTT (Liu and Schubert, *J Neurochem,* 69: 2285–2293, 1997) the high concentrations of antioxidants present in NB-B27 may compromise the usefulness of the MTT/MTS reduction assay for analysis of neurotoxicity in neuronal cultures maintained in NB-B27.

In addition to media that are serum-free, other investigators have used serum-containing media to support primary cultures of granule cells. The serum-containing media usually include undefined amounts of growth factors, steroids or other components that can influence viability, growth and differentiation of these cells. Ultimately, serum-containing media may not provide sufficiently well controlled study conditions for detection of modest, but biologically important, effects.

Each of these references describe a medium that contains extraneous components that may complicate studies aimed at elucidating the role of steroids during neuronal development, or how steroids regulate the functional properties of neurotransmitter receptors. As a result, studies aimed at defining factors that influence those processes are made more difficult when neurons are maintained in a culture medium containing undefined components. The limitations of the prior art are overcome by the present invention as described below. References mentioned in this background section are not admitted to be prior art with respect to the present invention.

BRIEF SUMMARY OF THE INVENTION

The present invention is directed to satisfying the need for a medium capable of allowing growth and development of neuronal cultures, without containing components which may interfere with bioassays. The present invention describes, but is not limited to use in the MTS and lactate dehydrogenase bioassays.

An embodiment of the invention comprises maintaining cerebellar granule neurons in a simplified serum-free medium lacking exogenous antioxidants, growth factors, and steroids or steroid-like compounds in a versatile 96-well culture plate format. The present invention is not limited to a 96-well culture plate, and can be practiced with other tissue culture vessels.

Chemically defined culture conditions, free of added antioxidants, serum and steroid hormones are established for the growth, maintenance and analysis of primary cultured granule cells in 96-well tissue culture plates. Results indicate that granule cell viability can be maintained for at least 3 weeks in defined granule cell serum free (GCSF) medium that consists of HEPES buffered DMEM supplemented with insulin, transferrin, selenium and depolarizing concentrations of KCl (25 mM). Elevated $K^+$ concentrations are used here because previous studies have indicated that the high concentrations of $K^+$ or activation of NMDA receptors mediate transient increases in intracellular $Ca^{++}$ concentrations that are required for maximal survival of cultured granule cells (Burgoyne et al., J Neurocytol., 22: 689–695, 1993).

The conditions set forth herein allows automated high-throughput analysis with the flexibility to employ many different bioassays, including the assessment of viability and cell death. Examples are given of the usefulness of these conditions with two methods frequently used to analyze neuronal toxicity; the MTT/MTS reduction assay to measure viability, and the LDH assay to measure cell death. The ability to easily maintain granule neurons under simple, well-defined conditions in 96-well plates provides a flexible and powerful model system that is suitable for rapidly determining the effects of various growth conditions, drugs, or toxicants on primary cultured neurons.

BRIEF DESCRIPTION OF THE SEVERAL VIEWS OF THE DRAWINGS

These and other features, objects and advantages of the present invention will become better understood from a consideration of the following detailed description and accompanying drawings.

DETAILED DESCRIPTION OF THE INVENTION

With reference to FIGS. 1–6, the preferred embodiment of the present invention may be described. Initial studies were performed to establish defined conditions for the maintenance of primary cultures of cerebellar granule neurons.

The results of our studies indicate that a relatively simple defined medium such as granule cell serum free (GCSF) medium, consisting substantially of HEPES buffered DMEM containing a final concentration of 25 mM glucose, 25 mM KCl, 0.5 mM glutamine, 5 $\mu$g/ml insulin and transferrin, 5 pg/ml selenium, and 1.5 mg/ml bovine serum albumin was capable of supporting a high-level of granule cell viability for at least 21 DIV.

When granule cells maintained in GCSF were plated, the cells were initially observed as well-dispersed single cells.

Figure 1A:
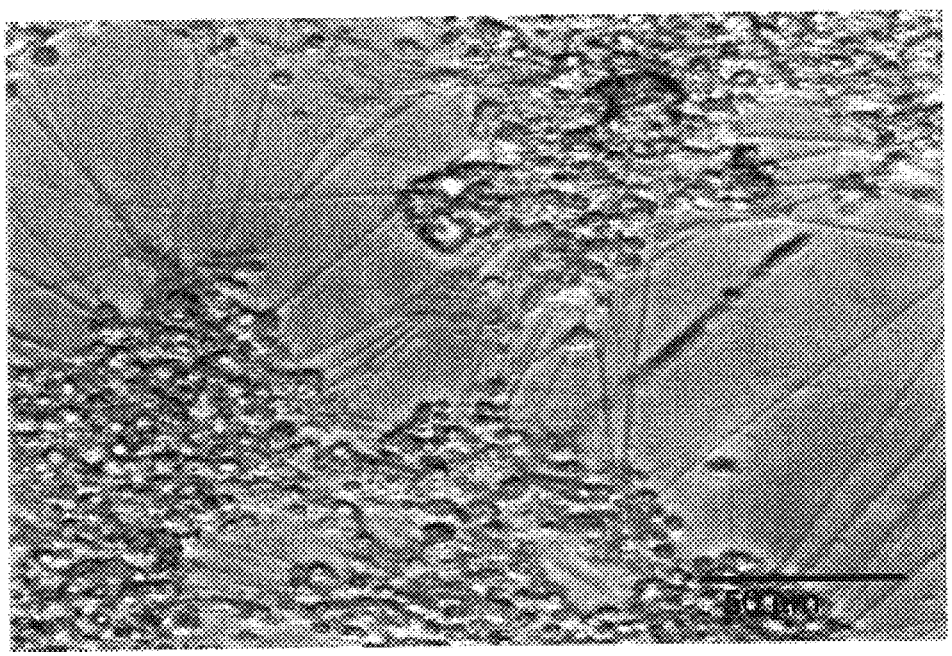
FIG. 1A is a low magnification, phase-contrast photomicrograph of primary cultures of neonatal rat cerebellar granule cell neurons. Cultures were maintained on poly-L-lysine coated 96-well tissue culture plates at $1 \times 10^5$ cells per well (0.32 $cm^2$) in GCSF for 7 days. Cultures consisted almost exclusively of the small (~5 $\mu$m diameter) granule cells that were observed in multicellular aggregates from which extensive networks of neurites are visible. Scale bar=50 $\mu$m.
Figure 1B:
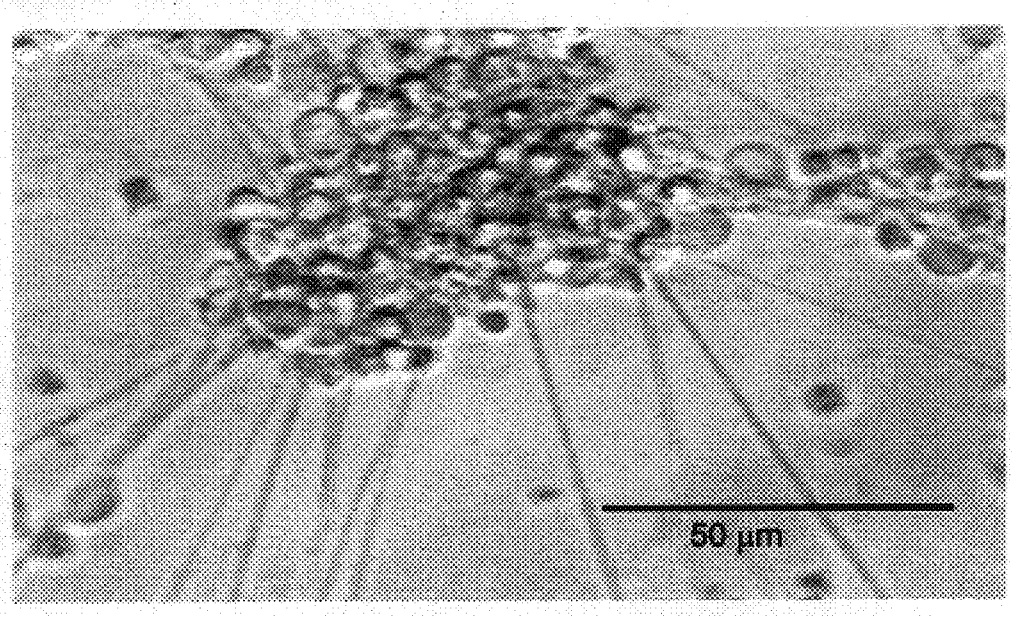
FIG. 1B is a high magnification, phase-contrast photomicrograph of primary cultures of neonatal rat cerebellar granule cell neurons. Cultures were maintained on poly-L-lysine coated 96-well tissue culture plates at $1 \times 10^5$ cells per well (0.32 $cm^2$) in GCSF for 7 days. Cultures consisted almost exclusively of the small (~5 $\mu$m diameter) granule cells that were observed in multicellular aggregates from which extensive networks of neurites are visible. Scale bar=50 $\mu$m.
Figure 2A:
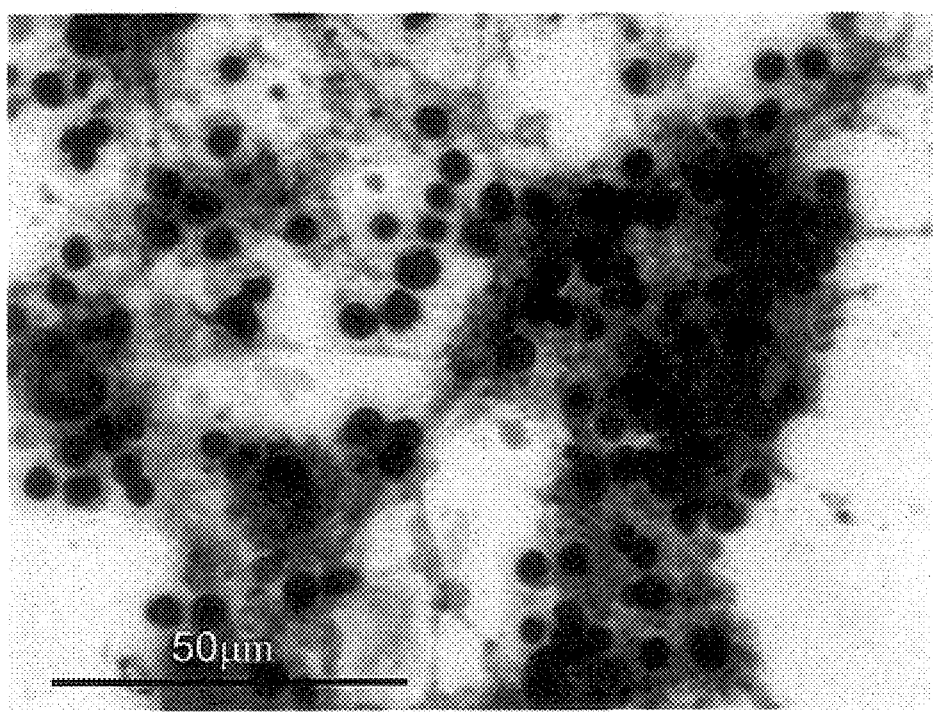
FIG. 2A is a photomicrograph of cerebellar cultures that were grown in GCSF containing 10 $\mu$M AraC. After 11 days in vitro primary cerebellar cultures that were grown in GCSF containing 10 $\mu$M AraC and stained with methylene blue were composed primarily of small granule cell neurons. Cultures were seeded at $3 \times 10^5$ cells/$cm^2$, maintained for the indicated number of days under the described conditions, fixed, and stained with 1% methylene blue. Scale bar=50 $\mu$m.
Figure 2B:
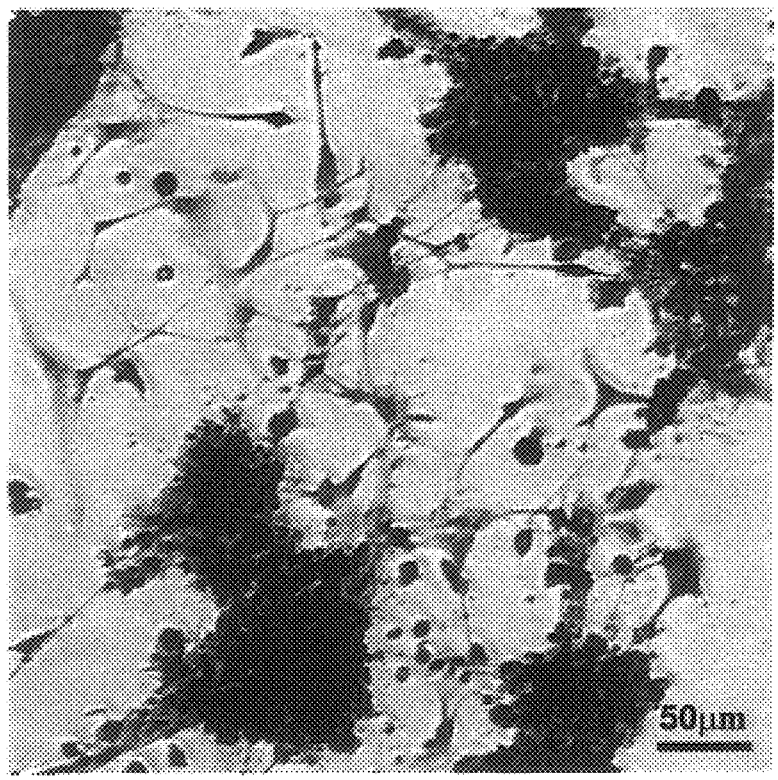
FIG. 2B is a photomicrograph of cerebellar cultures that were grown in GCS lacking AraC. After 11 days in vitro primary cerebellar cultures that were grown in GCSF lacking AraC, contained numerous glia-like non-neuronal cells which were interspersed with clusters of granule cells. Cultures were seeded at $3 \times 10^5$ cells/$cm^2$, maintained for the indicated number of days under the described conditions, fixed, and stained with 1% methylene blue. Scale bar=50 $\mu$m.
Figure 2C:
FIG. 2C is a photomicrograph of cerebellar cultures that were grown in NB-B27 without AraC for 14 days. After 14 days in vitro primary cerebellar cultures which were grown in NB-B27, fixed and immunostained for GFAP, revealed that numerous GFAP immunopositive non-neuronal cells were present. Scale bar=50 $\mu$m.
Figure 2D:
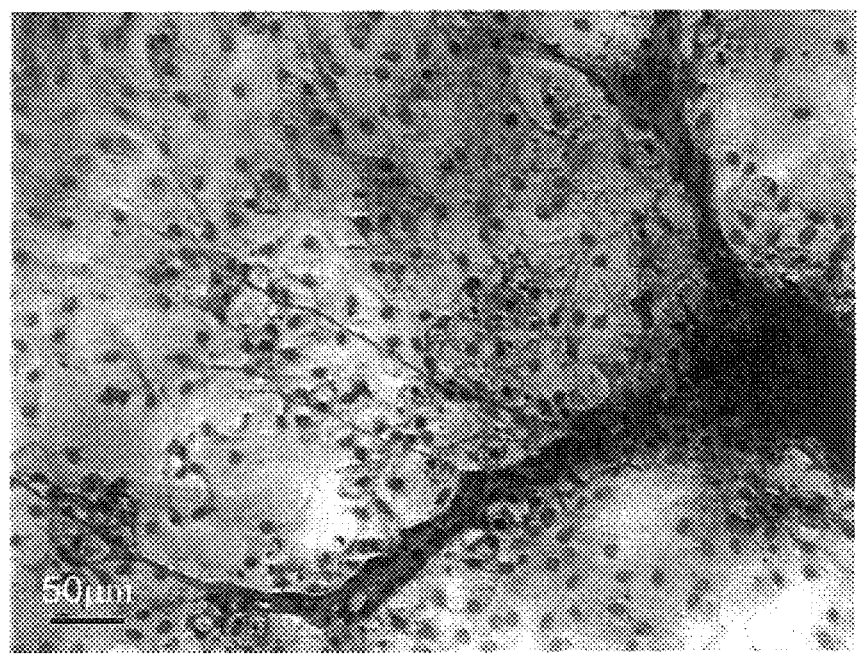
FIG. 2D is a photomicrograph of cerebellar cultures that were grown in NB-B27 without AraC for 30 days. Cultures grown in NB-B27 without AraC for 30 days were composed exclusively of a dense layer of large glia-like cells. Cultures were seeded at $3 \times 10^5$ cells/$cm^2$, maintained for the indicated number of days under the described conditions, fixed, and stained with 1% methylene blue. Scale bar=50 $\mu$m.
Figure 2E:
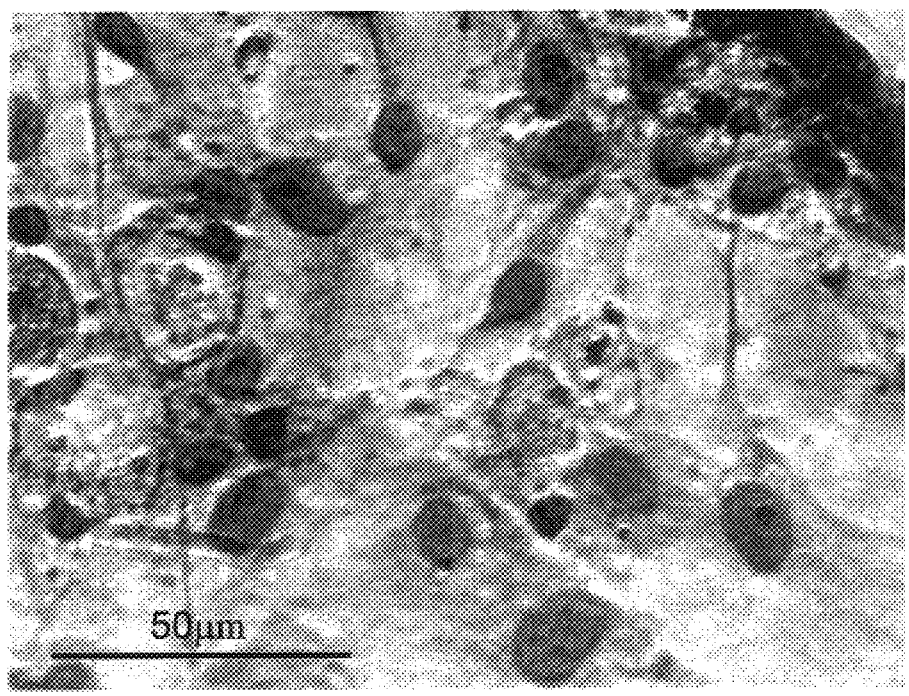
FIG. 2E is a photomicrograph of cerebellar cultures that were grown in NB-B27 without AraC for 30 days. Cultures grown in NB-B27 without AraC for 30 days were composed exclusively of a dense layer of large glia-like cells. Cultures were seeded at $3 \times 10^5$ cells/$cm^2$, maintained for the indicated number of days under the described conditions, fixed, and stained with 1% methylene blue. Scale bar=50 $\mu$m.

By 7 days in vitro (DIV), the majority of viable granule cells had migrated into aggregates from which extensive networks of processes emanated (FIGS. 1A–B). The morphology of the granule cells grown in GCSF was consistent with the phenotype expected of mature cultured granule cells and was similar to cells grown in NB-B27 or serum containing medium.

Previous studies have reported that proliferation of non-neuronal cell-types was blocked by the low concentrations of glutamine present in NB-B27 (Brewer, et al., *J Neurosci Res.* 35: 567–576, 1993; Carroll et al., *Neurochem. Int.* 33: 23–28, 1998). However, we observed proliferation of GFAP-immunopositive non-neuronal cell-types in cultures maintained in NB-B27 and also under GCSF conditions. Because both media contain low glutamine (0.5 mM), the rate of proliferation in either condition was markedly slower than in cultures supplemented with 10% serum. Nevertheless, after 2–3 weeks in vitro, a monolayer of glia-like cells was observed in cultures that lacked the anti-mitotic agent cytosine β-D-arabinofuranoside (AraC).

To inhibit proliferation of non-neuronal cells, a final concentration of 10 µM AraC was added to cultures after 24 hour in vitro. In cultures maintained in NB-B27 or GCSF and AraC, phase-contrast microscopic inspection of living (FIGS. 1A–B) or fixed cultures stained with methyl blue (FIG. 2A) revealed that cultures consisted almost exclusively of small granule cell neurons. Cultures maintained in the presence of AraC contained less than 5% non-neuronal cell types without a detectable loss of granule cell viability.

In contrast, if cerebellar cultures were maintained for more than 1 week in NB-B27 or GCSF without added AraC, increasing numbers of non-neuronal cell types were observed, and by 30 DIV cultures were devoid of granule cells and were comprised of a monolayer of non-neuronal cells (FIGS. 2B–E). Because of the apparent slow rate of glial mitosis, the most likely explanation for the difference in glial proliferation observed in our cultures is that we assessed the glial contamination following 2–4 weeks in culture rather than following 5 to 7 days in culture as was done previously (Brewer, et al., *J Neurosci Res.* 35: 567–576, 1993; Carroll et al., *Neurochem. Int.* 33: 23–28, 1998).

Immunocytochemical staining with antiserum specific for the glia specific marker GFAP, indicated that the majority of the non-neuronal cells were GFAP immunopositive (FIG. 2C) and are likely to have arisen from cerebellar glia present at the time of seeding.

We have also shown that granule cells cultured in GCSF could be maintained in 96-well tissue culture plates. The 96-well culture plate was chosen because: 1) this format affords easy automation of sample treatment and analysis; 2) 96-well plates are compatible with many different types of bioassays; 3) only a small number of cells are required for each sample which decreases the number of animals necessary for each experiment; and 4) a large number of individual samples can be simultaneously treated and analyzed thus increasing the statistical power of each experiment. A visual comparison of cultures seeded at densities ranging from $6.25 \times 10^3$ to $4.0 \times 10^5$ cells per well (0.32 cm$^2$) and maintained for 7 DIV in GCSF was performed. The comparison revealed that the viability and morphology of granule cells was not influenced by whether they were grown in 60 mm dishes or maintained in 96-well plates. Depending on the sensitivity of the end-point assay being employed, it is likely that the size of these granule cell cultures can be decreased to the 384 well format to increase further throughput capacity and associated advantages of this system.

Figure 3:
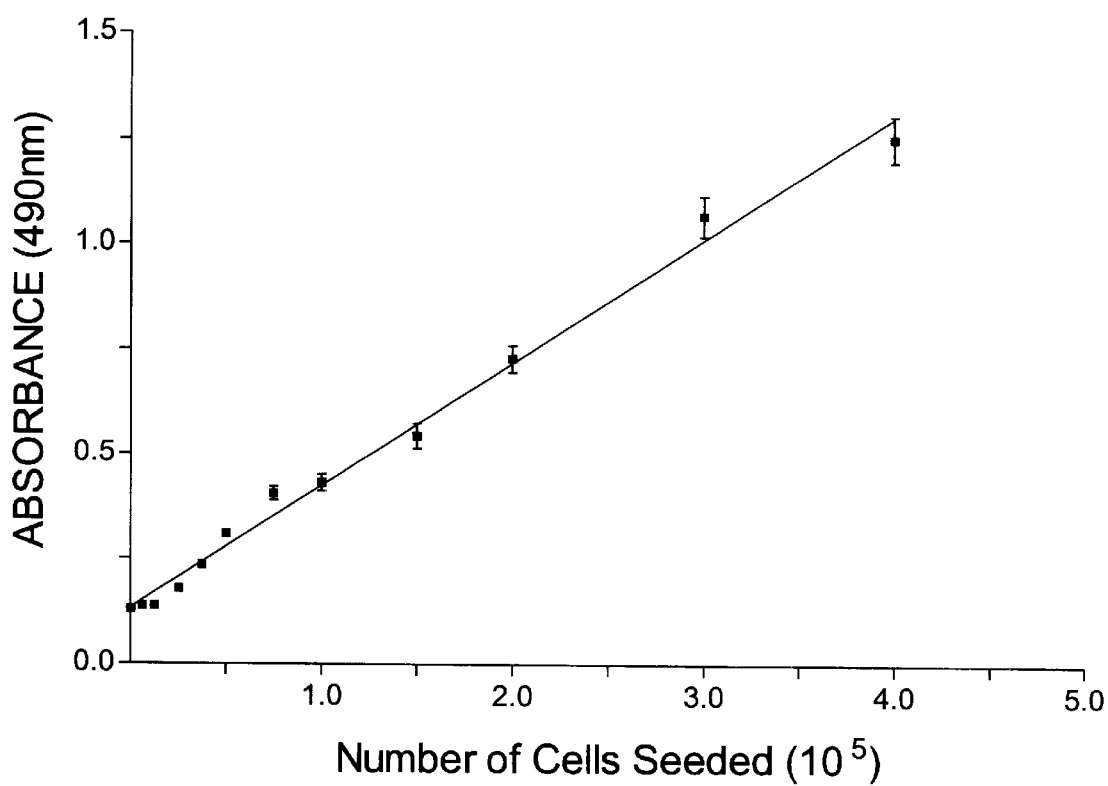
FIG. 3 is a graph of granule cell viability following 7 days in primary culture: MTS reduction. Viability was measured by MTS reduction in granule cell cultures seeded into 96-well tissue culture plates at initial densities ranging from $2 \times 10^4$ to $1.25 \times 10^6$ cells/$cm^2$. The amount of reduced MTS-formazan product generated in each sample was quantified spectrophotometrically at 490 nm and plotted as a function of the number of cells plated in each well. The linear regression for the data is indicated with the $r^2$ values for samples being 0.99. Samples from male and female pups were initially analyzed separately and found not to be significantly different. The presented data are of the averaged results from both males and females and are representative of at least three different experiments for each sex.
Figure 4A:
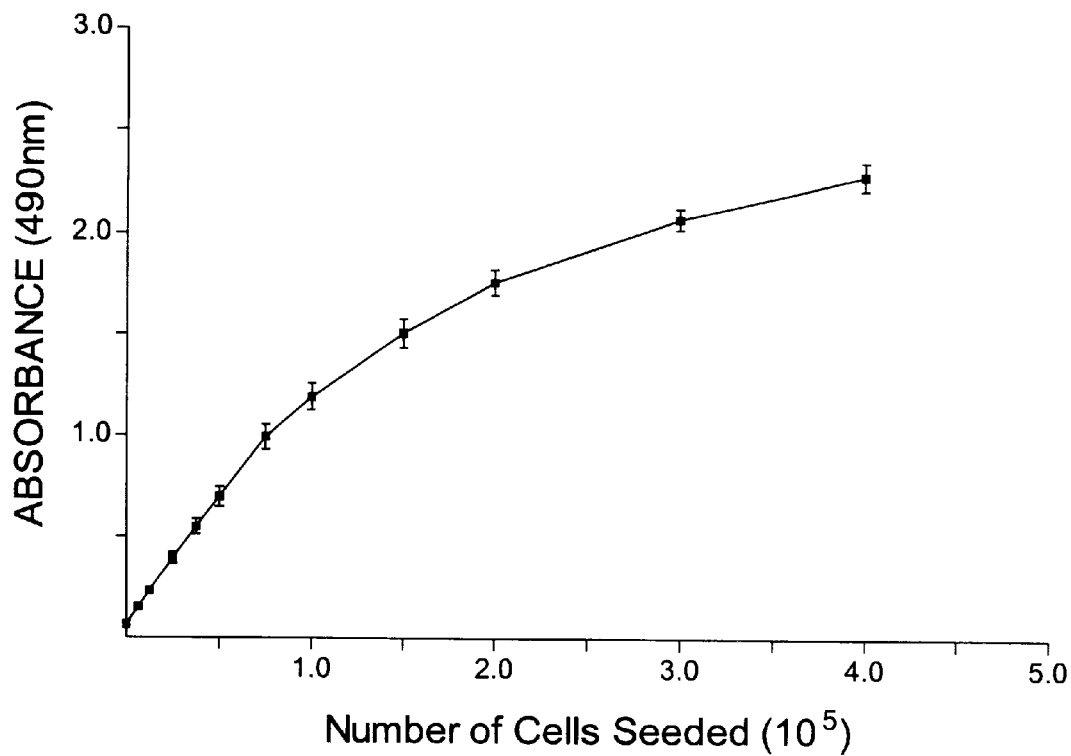
FIG. 4A is a graph of absorbance versus the number of granule cells seeded. The amount of LDH released into the culture media for the same samples that were analyzed by MTS-reduction assay was determined spectrophotometrically at 490 nm and plotted as a function of the number of cells plated in each well. The relative amount of LDH released parallels the number of cells seeded in each well, but plateaus above seeding densities of $2.0 \times 10^5$ cells per well. Samples from male and female pups were not significantly different; therefore the presented results are the averaged results from both males and females and are representative of at least three different experiments from each sex.
Figure 4B:
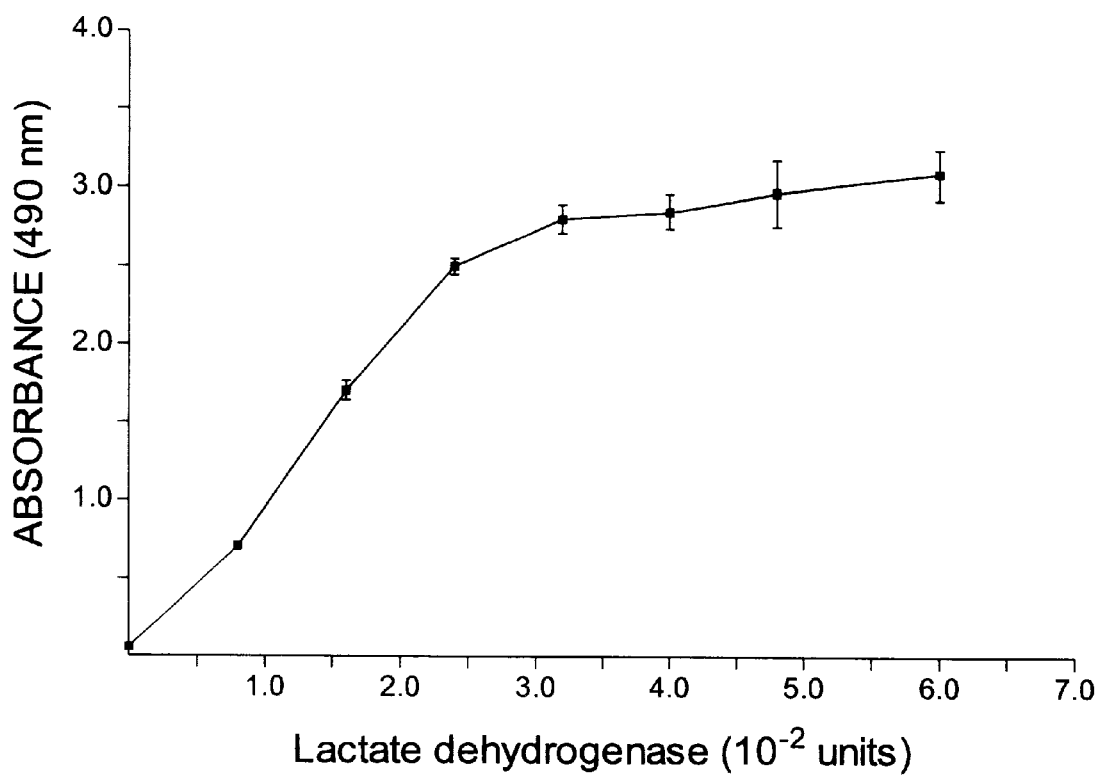
FIG. 4B is a graph of spontaneous LDH release by granule cells cultured in GCSF for 7 days. The LDH activity of known activities of purified bovine heart LDH was determined spectrophotometrically at 490 nm by the LDH release assay. Average $A_{490}$ values, plotted as a function of LDH activity, were proportional to the amount of LDH activity below 300 units of LDH. A significant deviation from linearity was observed above $A_{490}$ values of 2.5. Results are representative of at least 3 experiments.

Using the reduction of MTS as an indicator of granule cell viability and the release of LDH as an indicator of cell death, we determined seeding density that were compatible with reliable automated analysis of granule cell viability and cell death from the same 96-well culture (FIGS. 3 and 4A–B). After 7 DIV, the viability of granule cells plated at different seeding densities was assessed using a commercially available MTS reduction assay.

As can be seen in FIG. 3, at seeding densities above $2.5 \times 10^4$ cells per well there is a linear correlation between the absorbance readings at 490 nm and the number of cells seeded. Because this assay is frequently employed to measure a decrease in viability following a toxic insult, the ability to reliably detect a decrease in MTS reduction required an initial seeding density of around $0.5-1 \times 10^5$ cells per well under the standard MTS assay conditions used. The results of the MTS assay for 7 DIV cultures seeded on the 96-well plates suggest a linear correlation between the absorbance readings at 490 nm and the number of cells seeded in each well.

The activity of the cytosolic enzyme lactate dehydrogenase released into media by cells that have lost cell membrane integrity, is frequently used as a measure of cell death (Choi and Koh, *Annul Rev Neurosci.* 21, 347–375, 1998). To determine the amount of spontaneous LDH release occurring in these cultures, samples of culture media were removed from the 7 DIV cultures prior to MTS analysis. Aliquots of each sample were analyzed using a commercially available colorimetric assay for LDH activity. In contrast to the results of the MTS assay, LDH release was linear at seeding densities below $1.0-1.5 \times 10^5$ cells per well with an obvious plateau at densities above $2.0 \times 10^5$ cells per well (FIG. 4A). Therefore, a plating density of $0.5-1.0 \times 10^5$ cells per well or less is required to reliably detect increased LDH release under the standard assay conditions employed here.

To determine whether the plateau observed in the LDH absorbance readings resulted from saturation of the LDH assay, a dilution series of known concentrations of purified bovine heart LDH was analyzed (FIG. 4B). Under the standard assay conditions, absorbance readings were saturated with $3.0 \times 10^{-2}$ units of LDH, indicating that under those conditions, the dynamic range for the assay was below $A_{490}$ values of 2.5–3.0. Because the LDH assay was not saturated at $A_{490}$ values below 2.0, it is likely that the plateau in spontaneous LDH release observed in granule cell cultures at $A_{490}$ values above 1.5 was not due to saturation of the LDH assay. Because it is well-known that viability of cultured neurons is increased at higher cell densities (Ahmed et al., *J Neurosci.*, 3, 2448–2462, 1983; Brewer and Cotman, *Brain Res.* 494, 65–74, 1989), the most likely explanation for the observed plateau in spontaneous LDH release is that at higher cell densities decreased necrotic cell death is occurring during the seven day culture period. Our analysis indicates there is a relatively narrow window of initial cell plating densities around $0.5-1.0 \times 10^5$ cells per well that is useful for simultaneous analysis of MTS reduction and LDH release from the same culture.

Viability of granule cell was determined by assessing the ability of living cells to endocytose and metabolically reduce the MTS compound, rather than the more frequently used MTT reduction assay. The MTS compound, which is chemically similar to the MTT tetrazolium salt, is reduced in living cells by endosomal or lysosomal dehydrogenases to the colored formazan product which is then exocytosed into the culture media (Liu et al., *J Neurochem,* 69: 581–593, 1997). Unlike the MTT formazan product, however, the MTS formazan product is soluble and stable in tissue culture medium (Cory et al., *Cancer Commun.,* 3: 207–212, 1991) and therefore does not require solubilization prior to spectrophotometric analysis. Along with avoiding the time consuming solubilization of the insoluble MTT-formazan, using the soluble MTS reagent avoids potential underestimates of viability that are associated with the extracellular accumulation of the insoluble MTT-formazan crystals. The accumulation of these insoluble crystals inhibits the reduction of additional MTT by interfering with the intracellular uptake of MTT and in some cases results in an overestimation of cell death (Liu and Schubert, *J Neurochem.,* 69: 2285–2293, 1997).

Figure 5A:
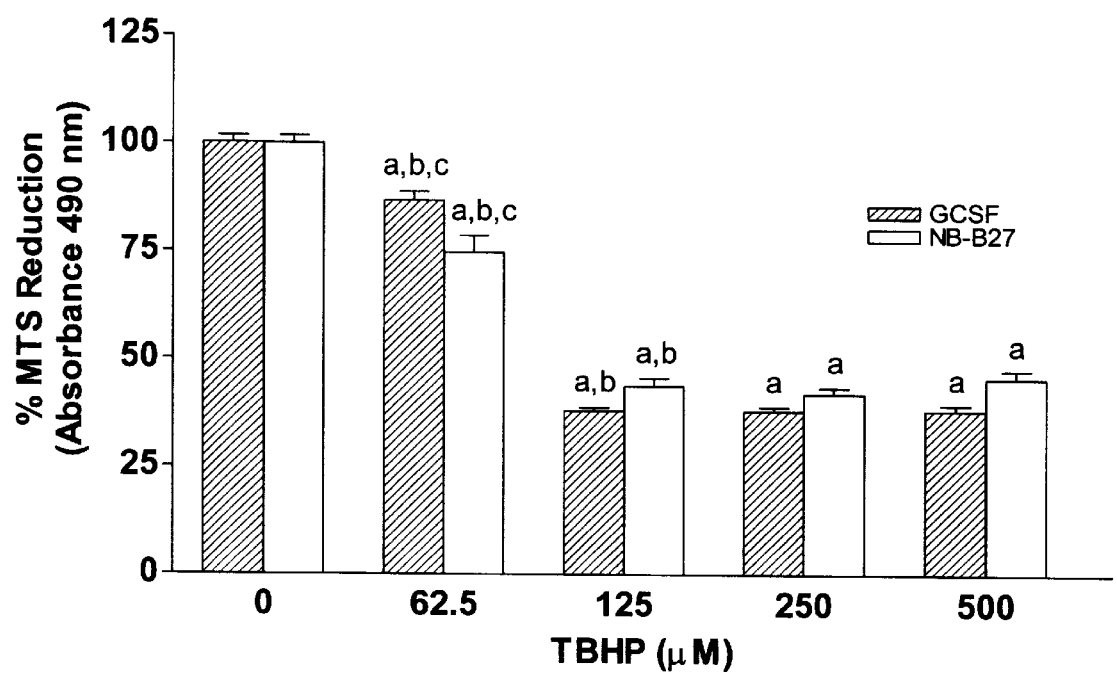
FIG. 5A is a graph analyzing MTS reduction for TBHP-treated granule cells cultured in GCSF or NB-B27. Oxidative stress was induced by exposure of 7 days in vitro (DIV) granule cell culture seeded at $1 \times 10^5$ per well to increasing concentrations of tert-butyl-hydroperoxide for 24 hours in GCSF or NB-B27 media. Changes in granule cell viability were determined independently from the same culture by analysis of MTS reduction. The results are expressed as a mean percentage±SEM from 3 separate experiments (n=16–32 per group) and level of significance between treatment groups was determined by one-way analysis of variance and the Neuman-Keul's multiple comparison method. "a" indicates that the value is significantly different from its respective controls ($p<0.001$). "b" indicates that the value is significantly different from preceding value ($p<0.001$). "c" indicates that the value for that treatment is significantly different between GCSF and NB-B27 media ($p<0.001$).
Figure 5B:
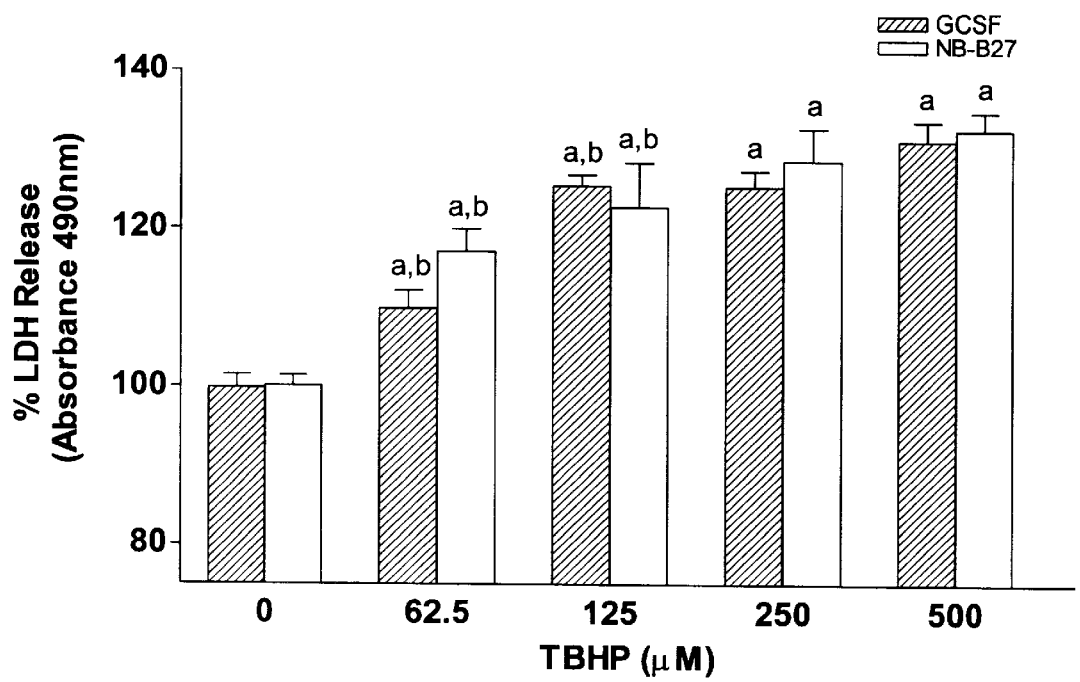
FIG. 5B is a graph analyzing LDH release for TBHP-treated granule cells cultured in GCSF or NB-B27. Oxidative stress was induced by exposure of 7 DIV granule cell culture seeded at $1 \times 10^5$ per well to increasing concentrations of tert-butyl-hydroperoxide for 24 hours in GCSF or NB-B27 media. Changes in granule cell viability were determined independently from the same culture by analyzing the release of LDH. The results are expressed as a mean percentage±SEM from 3 separate experiments (n=16–32 per group) and level of significance between treatment groups was determined by one-way analysis of variance and the Neuman-Keul's multiple comparison method. "a" indicates that the value is significantly different from its respective control ($p<0.001$ except the value for 62.5 $\mu$M TBHP in GCSF where $p<0.05$). "b" indicates that the value is significantly different from the preceding value (for GCSF treatment groups $p<0.05$ for 62.5 $\mu$M and $p<0.01$ for 125 $\mu$M TBHP and for NB-B27 treatment groups $p<0.001$ for 62.5 $\mu$M and P<0.05 for 125 $\mu$M TBHP).
Figure 5C:
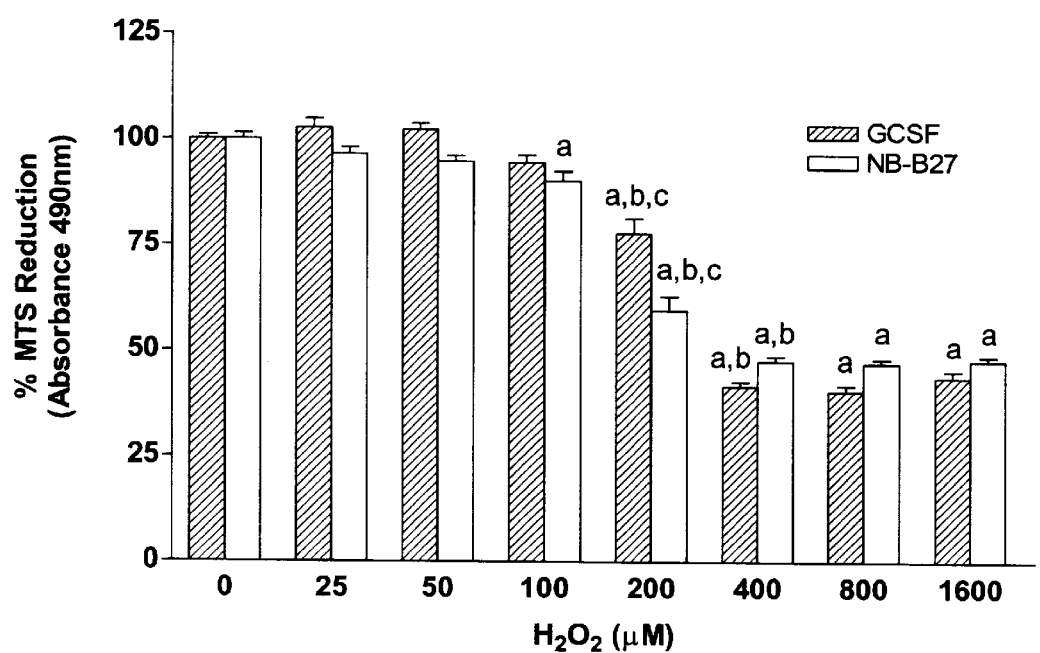
FIG. 5C is a graph analyzing MTS reduction for $H_2O_2$-treated granule cells cultured in GCSF or NB-B27. Oxidative stress was induced by exposure of 7 DIV granule cell culture seeded at $1 \times 10^5$ per well to increasing concentrations of hydrogen peroxide for 24 hours in GCSF or NB-B27 media. Changes in granule cell viability were determined independently from the same culture by analysis of MTS reduction. The results are expressed as a mean percentage±SEM from 3 separate experiments (n=16–32 per group) and level of significance between treatment groups was determined by one-way analysis of variance and the Neuman-Keul's multiple comparison method. "a" indicated that the value is significantly different than the respective control value ($p<0.001$). "b" indicates that the value is significantly different from the preceding value ($p<0.001$). "c" indicates that the value for that treatment is significantly different between GCSF and NB-B27 media ($p<0.001$ at 200 $\mu$M $H_2O_2$ and $p<0.05$ at 800 $\mu$M $H_2O_2$).
Figure 5D:
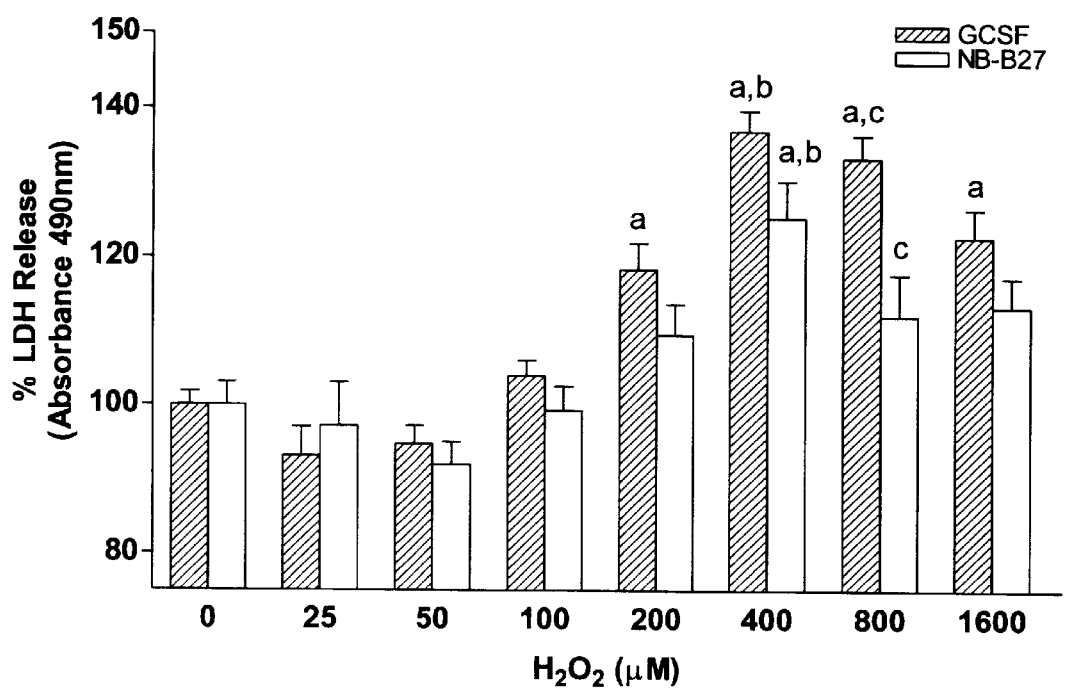
FIG. 5D is a graph analyzing LDH release for $H_2O_2$-treated granule cells cultured in GCSF or NB-B27. Oxidative stress was induced by exposure of 7 DIV granule cell culture seeded at $1 \times 10^5$ per well to increasing concentrations of hydrogen peroxide for 24 hours in GCSF or NB-B27 media. Changes in granule cell viability were determined independently from the same culture by analysis of MTS reduction. The results are expressed as a mean percentage±SEM from 3 separate experiments (n=16–32 per group) and level of significance between treatment groups was determined by one-way analysis of variance and the Neuman-Keul's multiple comparison method. "a" indicates that the value is significantly different from the respective control ($p<0.001$ with the exception of the GCSF 200 $\mu$M $H_2O_2$ treatment group where $p<0.05$). "b" indicates that the value is significantly different from the preceding value (in GCSF $p<0.01$ and in NB-B27 $p<0.05$). "c" indicates that the value for the 800 $\mu$M treatment group is significantly different between GCSF and NB-B27 media ($p<0.01$).

To demonstrate the usefulness of the GCSF culture system for analysis of oxidative-stress using the MTS and LDH assays was demonstrated by determining the dose-dependence of TBHP-and $H_2O_2$-induced granule cell toxicity in cultures grown in GCSF and NB-B27 (FIGS. 5A–D). In general, major differences between culture conditions were not observed; however small but significant differences between cultures maintained in GCSF and NB-B27 were detected by MTS-reduction analysis in the 200 $\mu$M $H_2O_2$ and 62.5 $\mu$M TBHP treatment groups (FIGS. 5A and 5C). Independent of culture condition, significant effects on granule cell viability/lysis were initially detected in the 200 $\mu$M $H_2O_2$ and 62.5 $\mu$M TBHP treatment groups, with maximal effects observed at concentrations of 400 $\mu$M $H_2O_2$ and 125 $\mu$M TBHP. At 400 $\mu$M $H_2O_2$ MTS-reduction was decreased to 41.5±1.0% of control in GCSF cultures and 47±1.2% of control in NB-B27. Whereas LDH-release was increased to 136.9±2.8% of control in GCSF cultures and 125±5.0% of control in NB-B27. Similarly, at 125 $\mu$M TBHP, MTS-reduction was decreased to 37.9±0.8% of control in GCSF cultures and 43.7±1.9% of control in NB-B27; LDH-release was increased to 125.4±1.4% of control in GCSF cultures and 122.7±5.6% of control in NB-B27 (FIGS. 5A–5D).

Using the MTS-reduction assay, we demonstrated that the cultured granule cells are susceptible to neurotoxic cell death induced by two neurotoxins that induce cell death by two different mechanisms. Exposure of cultures to oxidative stress or excitotoxic concentrations of glutamate resulted in significant levels of granule cell death as indicated by decreased MTS reduction or LDH release compared to mock treated cultures. While slight differences could be detected, the dose-dependence of oxidative neuronal injury induced by $H_2O_2$ and TBHP were similar in cultures grown in GCSF or NB-B27. Compared to NB-B27 and other serum-free conditions, the lack of steroid or exogenous antioxidants in GCSF granule cell culture model has distinct advantages for neurotoxicological and neurodevelopmental studies.

To demonstrate that statistically significant results may be obtained from a single experiment and to demonstrate usefulness of this culture system for analysis of excitotoxicity, the effects of L-glutamate exposure were measured in cultures with the MTS reduction assay. As is demonstrated by the results of a representative experiment (FIG. 6), exposure of cultured granule cell to 500 $\mu$M L-glutamate decreased granule cell viability to 56.8±2% of control cultures. This decrease in MTS reduction is similar to the average maximal decrease in viability (56±5% of control) observed in cultures following treatment with the $Ca^{2+}$ ionophore ionomycin.

Figure 6:
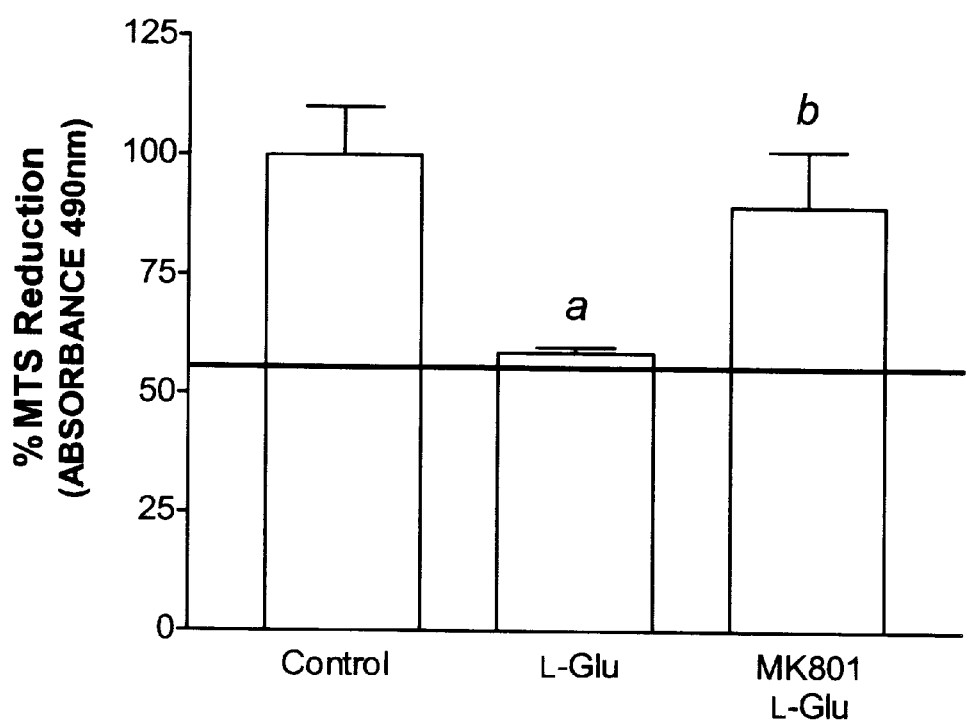
FIG. 6 is a graph of glutamate induced granule cell toxicity and MK801 antagonism of excitotoxicity. Neuronal toxicity was induced by exposure of 7 DIV granule cell cultures that were seeded at $1 \times 10^5$ cells per well to 500 $\mu$M L-Glutamate or 100 $\mu$M $H_2O_2$ for 24 hours in GCSF media. The ability of the NMDA receptor antagonist MK-801 to attenuate L-glutamate induced excitotoxicity was determined in cultures pretreated with 10 $\mu$M MK-801 prior to the L-glutamate exposure. Following neurotoxin exposure, granule cell viability was determined by the MTS reduction assay. Results of an individual representative single experiment from one 96-well plate are shown. Statistically significant levels of neuronal cell death were observed in the $H_2O_2$ and L-glutamate treated samples. Cultures pretreated with MK-801 were significantly protected from L-glutamate induced excitotoxicity. A level of significance was determined by one-way analysis of variance and Tukey multiple comparison method (n=8 per group). "a" indicates that the results are significantly different from control treatment ($p<0.01$); "b" indicates that the results are significantly different from L-glutamate treatment ($p<0.05$) and not significantly different from control treatment. The average maximal reduction in granule cell viability obtained in cultures with 10 nM ionomycin is indicated with a dashed line.

We also demonstrate that pretreatment of cultures with the NMDA receptor antagonist MK-801 prior to glutamate exposure blocked the majority of excitotoxicity. A significant level of neuroprotection was observed in cultures that were pretreated with 10 $\mu$M of the NMDA receptor antagonist MK-801. Viability of those cultures was not significantly different from the mock-treated control cultures (FIG. 6). The levels of L-glutamate induced excitotoxicity and MK-801 protection were similar to those observed in cultures of murine granule cells (Carroll et al., *Neurochem Int,* 33: 23–28, 1998). These results clearly demonstrate the usefulness of this neuronal culture system for rapidly detecting statistically significant changes in neuronal viability from a single experiment.

In summary, we have developed a defined neuronal culture system that lacks supplemental serum, steroid hormones, and antioxidants with distinct advantages for examining neurotoxic, neurotrophic or mitogenic influences of potential drugs or toxicants. Overall, the advantages of this defined neuronal culture system includes the ability to rapidly and simultaneously measure different experimental manipulations in multiple samples and a resulting increased potential to detect modest, but biologically relevant effects.

EXAMPLES

Example 1

Cerebellar Culture Medium Preparation

Serum-free granule cell culture medium (GCSF) lacking phenol red was composed of 1× Dulbecco's Modified Eagle Medium (DMEM), 25 mM glucose, 26 mM $NaHCO_3$, 0.23 mM sodium pyruvate (GIBCO/BRL, Rockville, Md.), buffered with 10 mM HEPES (Sigma, St. Louis, Mo.) and adjusted to pH 7.2. The HEPES buffered DMEM was supplemented with 0.5 mM L-glutamine, 20 mM KCl (final concentration 25 mM), 0.37 mM bovine albumin (fraction V; USB, Cleveland, Ohio), 5 $\mu$g/ml insulin, 5 $\mu$g/ml transferrin, 5 $\mu$g/ml selenium (BioWhittaker, Walkersville, Md.), 100 units/ml penicillin, and 100 $\mu$g/ml streptomycin (GIBCO/BRL).

Example 2

Cerebellar Cell Isolation and Primary Culture Conditions

Cerebella were isolated from postnatal day 7–9 (P7–P9) male or female Sprague-Dawley rat pups. Following rapid dissection, the cerebellum was immediately immersed in ice-cold culture medium and meninges were gently removed from the cerebellar surface. Each cerebellum was placed into 2–5 ml of fresh media, chopped finely with a sterile scalpel blade and cerebellar cells were dissociated by trituration through a fire-polished Pasteur pipette. Dissociated cells were filtered through a 40 $\mu$M nylon cell strainer (Falcon, Franklin Lakes, N.J.) to remove any remaining clumps of cells. The final volume of the resulting single cell suspension was adjusted to 10 ml. The number of viable cells was determined by counting trypan blue dye-excluding cells using Neubauer hemacytometer. The resulting cell yield from rat pups with body weight ranging from 16.5–19.0 g averaged 6.5×10$^6$ cells per cerebellum.

Based on the calculated cell numbers, cerebellar cells were serially diluted in an appropriate volume of culture media and seeded into flat-bottom 96-well tissue culture plates pre-coated with poly-L-lysine (Becton Dickinson, Bedford, Mass.). The numbers of cerebellar cells seeded ranged from 6,250 to 400,000 cells per well (0.32 cm$^2$) in a final volume of 200 $\mu$l. Cultures were maintained in a humidified incubator in 5% $CO_2$ at 37° C. After 24 hours in culture, a final concentration of 10 $\mu$M cytosine $\beta$-D-arabinofuranoside (AraC; Sigma) was added to each well to inhibit proliferation of non-neuronal cells. Under these conditions, visual inspection of cultures indicated that >90% of the cells present had a morphological phenotype expected for the small cerebellar granule cell neurons (FIG. 1).

Example 3
Cerebellar Cell Staining and Immunocytochemistry

Cerebellar cells were prepared as described above, seeded at $5 \times 10^5$ cells per well (0.32 cm$^2$) poly-L-lysine coated 4-well chamber slides, and cultured without added serum in GCSF or NB-B27 supplement with or without 10 µM AraC. After 7–30 day in vitro, cultures were washed 3 times with phosphate buffered saline (PBS) and fixed for 20–30 minutes with 4% paraformaldehyde in 0.1M sodium phosphate buffer (pH 7.4; PB). Following fixation, cells were washed 3 times with PBS, and either stained with 1% methylene blue (Sigma) in deionized water for 5 minutes and destained with deionized water or permeablized for immunostaining with 0.2% Triton X-100 in PBS. Permeablized cells were washed 3 times with PBS, incubated for 1 hour in 5% normal horse serum in PB and then incubated overnight at 4° C. with a glial fibrillary acidic protein (GFAP) antiserum (1:5000 dilution; Dako, Carpintea, Calif.). Following incubation with primary antiserum, cells were extensively washed with PBS plus 0.1% Tween-20 and immunoreactivity was visualized with NiCl/3,3'-diaminobenzidine (DAB) using the avidin-biotin-complex (ABC) method (Vector Elite-universal; Vector Laboratories, Burlingame, Calif.). Extensive washing with deionized H$_2$O terminated peroxidase reactions. Images were acquired using a Hamamatsu CCD camera attached to a Zeiss Axioskop microscope. Following acquisition, digital images were transferred to PhotoShop 5.5 (Adobe) for generation of graphics.

Example 4
MTS Assay

Viability of the cerebellar granule cell culture was assessed using CellTiter 96® AQ$_{ueous}$ One Solution Cell Proliferation reagent (Promega, G3580). This colorimetric assay employs, 3-(4,5-dimethylthiazol-2-yl)-5-(3-carboxymethoxyphenyl)-2-(4-sulfophenyl)-2H-tetrazolium (MTS) and the electron coupling reagent, phenazine ethosulfate (PES). Like the well-known MTT assay (Mosmann, J Immunol Methods, 65:55–63, 1983; Hansen et al., J Immunol Methods, 1 19: 203–210, 1989), metabolically active cells reduce the MTS compound and the amount of the resulting colored formazan product is proportional to the number of viable cells. Unlike MTT, the MTS formazan product is soluble and stable in tissue culture medium (Cory et al., Cancer Commun 3:207–212, 1991) and therefore does not require solubilization prior to measuring the absorbance at 490 nm. Briefly, prior to each MTS assay, 100 µl of media was removed from each well, transferred to new 96-well plate for subsequent LDH release analysis. To each cell containing well, 20 µl of MTS tetrazolium reagent was added to the remaining media (100 µl). Culture plates were incubated in the humidified incubator at 37° C. and in 5% CO$_2$ for 2 hours. Following incubation the quantity of formazan product present was determined by measuring the absorbance at 490 nm using a VERSAmax® microplate reader and SOFTmax PRO software (Molecular Devices).

Example 5
LDH Release Assay

The lactate dehydrogenase (LDH) released into the media was determined using Cyto Tox96® non-radioactive cytotoxicity assay (Promega). In this calorimetric assay, LDH converts lactate and nicotinamide adenine dinucleotide (NAD$^+$) to pyruvate and NADH, respectively. This initial reaction is coupled to a second reaction where diaphorase converts iodo-nitro-tetrazolium salt and NADH to a red colored formazan compound and NAD$^+$ respectively. Briefly, 50 µl of assay buffer was added to each 100 µl sample of media removed from each well prior to MTS analysis. Samples were then incubated in the dark for 30 minutes at room temperature, and then 50 µl of a stop solution (1M acetic acid) was added into each well and the absorbance at 490 nm was measured as above. Positive control samples of bovine heart LDH (800 units/ml; lot 11455502, Promega) were serially diluted into a final volume of 200 µl and assayed as described above.

Example 6
Analysis of Neurotoxicity

Granule cell cultures were seeded at an initial density of $1 \times 10^5$ cells per well and maintained in GCSF culture media for 7 day in vitro prior to toxicant exposure. On the day of treatment, L-Glutamate, tert-butyl-hydroperoxide (TBHP), hydrogen peroxide (H$_2$O$_2$), ionomycin (Sigma), and MK-801 (Calbiochem, San Diego) were prepared at required concentration in the appropriate media. Cultures were exposed to toxicants for 24 hours prior to viability analysis. Cultures receiving MK-801 were pretreated for 10 minutes prior to addition of L-glutamate, and negative control cultures were treated with fresh media. For dose-dependence of oxidative-induced injury H$_2$O$_2$ and TBHP stock solutions were serially diluted in media to 100× concentrations immediately before each experiment. The concentration of the H$_2$O$_2$ stock solution was determined spectrophotometrically before each experiment based on its absorbance using the equation: $C=(Ab_{240}/\epsilon) \times DF$; where C is the concentration of H$_2$O$_2$ (mM), Ab$_{240}$ is absorbance at 240 nm, $\epsilon$ is the extinction coefficient (0.0394 mM$^{-1}$ cm$^{-1}$), DF is the dilution factor, and the path-length of the spectrophotometer is 1 cm. Comparative analysis of granule cell viability/lyses in GCSF and NB-B27 was assessed using the MTS reduction and LDH release assays as described above.

Example 7
Statistical Analysis

All data presented is representative of at least 3 independent experiments. Individual experiments were performed in a single 96-well plate containing appropriate negative (media blank and vehicle) and positive (untreated, purified LDH or ionomycin) controls. Within each experiment, data from an individual well was treated as a single data point. Statistical analysis was conducted by one-way analysis of variance (ANOVA) and post-test comparison performed using Newman-Keul's and Tukey's multiple comparison methods. Unless otherwise noted, a level of statistical significance is considered $p<0.05$. Data was analyzed with Excel 97 (Microsoft Corp.) and GraphPad Prism® version 3.0 (GraphPad Software Inc., San Diego).

The present invention may be used for, but is not limited to, drug discovery, identification of steroidal or non-steroidal factors that influence neuronal development, identification of steroidal or non-steroidal factors that spare neurons from death following hypoxic-ischemic insult, identification of steroidal or non-steroidal factors that spare neurons from death following excitotoxic insult, identification of steroidal or non-steroidal factors that spare neurons from death following exposure to reactive oxygen species, and toxicological screening.

The present invention has been described with reference to certain preferred and alternative embodiments that are intended to be exemplary only and not limiting to the full scope of the present invention as set forth in the appended claims.

What is claimed is:

1. A serum-free and steroid-free cultural medium for growth and analysis of neurons, consisting essentially of:

a. a defined basal medium;
b. a supplemental carbohydrate, wherein the carbohydrate is present at a concentration between 1% and 5% weight/volume (w/v);
c. a supplemental buffer, such that the pH of the culture medium is between pH 7.0 and pH 7.6;
d. insulin;
e. transferrin;
f. selenium;
g. L-glutamine; and
h. bovine albumin.

2. The medium of claim 1, further including a potassium salt.

3. The medium of claim 2 wherein said potassium salt is potassium chloride.

4. The medium of claim 3, wherein said potassium chloride is at a concentration of around 0 mM to around 25 mM.

5. The medium of claim 1, further including penicillin.

6. The medium of claim 1, further including streptomycin.

7. The medium of claim 1, further including β-D-arabinofuranoside.

8. The medium of claim 1 wherein said medium is essentially free of phenol red.

9. The medium of claim 1 wherein said medium is essentially free of growth factors.

10. The medium of claim 1 wherein said medium is essentially free of steroids.

11. The medium of claim 1 wherein said defined basal medium is Dulbecco's Modified Eagle Medium (DMEM).

12. The medium of claim 1 wherein said supplemental carbohydrate is glucose.

13. A serum-free and steroid-free cultural medium for growth and analysis of neurons, consisting essentially of:
    a. Dulbecco's Modified Eagle Medium (DMEM);
    b. glucose at a concentration between 1% and 5% weight/volume (w/v);
    c. HEPES at a concentration such that the pH of the culture medium is effectively buffered between pH 7.0 and pH 7.6;
    d. insulin;
    e. transferrin;
    f. selenium;
    g. L-glutamine; and
    h. bovine albumin.

14. The medium of claim 13, further including potassium chloride.

15. The medium of claim 14, wherein said potassium chloride is at a concentration of around 0 mM to around 25 mM.

16. The medium of claim 13, further including penicillin.

17. The medium of claim 13, further including streptomycin.

18. The medium of claim 13, further including β-D-arabinofuranoside.

19. The medium of claim 13 wherein said medium is essentially free of phenol red.

20. The medium of claim 13 wherein said medium is essentially free of growth factors.

21. The medium of claim 13 wherein said medium is essentially free of steroids.

22. A serum-free and steroid-free cultural medium for growth and analysis of neurons, consisting essentially of:
    a. Dulbecco's Modified Eagle Medium (DMEM);
    b. glucose at a concentration between 1% and 5% weight/volume (w/v);
    c. HEPES at a concentration such that the pH of the culture medium is effectively buffered between pH 7.0 and pH 7.6;
    d. insulin;
    e. transferrin;
    f. selenium;
    g. L-glutamine;
    h. bovine albumin; and
    i. β-D-arabinofuranoside.

23. The medium of claim 22, further including potassium chloride.

24. The medium of claim 23, wherein said potassium chloride is at a concentration of around 0 mM to around 25 mM.

25. The medium of claim 22, further including penicillin.

26. The medium of claim 22, further including streptomycin.

27. The medium of claim 22 wherein said culture medium is essentially free of phenol red.

28. The medium of claim 22 wherein said culture medium is essentially free of growth factors.

29. The medium of claim 22, wherein said culture medium is essentially free of steroids.

30. A serum-free and steroid-free cultural medium for growth and analysis of neurons, consisting essentially of:
    a. Dulbecco's Modified Eagle Medium (DMEM);
    b. glucose at a concentration of 4.5% weight/volume (w/v);
    c. HEPES at a concentration such that the pH of the culture medium is 7.5;
    d. insulin;
    e. transferrin;
    f. selenium;
    g. L-glutamine;
    h. potassium chloride;
    i. bovine albumin;
    j. β-D-arabinofuranoside;
    k. penicillin; and
    l. streptomycin.

31. A method for culturing neurons for high throughput analysis comprising the steps of:
    a. isolating neurons;
    b. maintaining neurons in the culture medium of claim 1;
    c. dissecting isolated neurons in the culture medium of claim 1 under conditions to obtain neuronal cells;
    d. filtering the neuronal cells;
    e. adding neuronal cells in an appropriate concentration to a culturing vessel;
    f. maintaining the neuronal cells in the culture medium of claim 1 in a carbon dioxide concentration between 3% and 10%;
    g. maintaining the neuronal cells in the culture medium of claim 1 in a humidity concentration around 100%; and
    h. maintaining the neuronal cells in the culture medium of claim 1 at a temperature of around 37° C.

32. The method of claim 31 further comprising the step, during step (b), of adding β-D-arabinofuranoside to the culture medium in an amount effective to inhibit the proliferation of non-neuronal cells.

33. The method of claim 31 wherein said culturing vessel comprises a tissue culture plate.

34. The method of claim 33 wherein said tissue culture plate is a 96-well plate.

35. The method of claim 33 wherein said tissue culture plate is a 384-well plate.

36. The method of claim 33 wherein said tissue culture plate is coated with poly L-lysine.

37. The method of claim 31 wherein said appropriate concentration of neuronal cells is from around $1.0 \times 10^4$ to around $3.2 \times 10^6$ cells per square centimeter.

38. The method of claim 31 wherein said appropriate concentration of neuronal cells is from around $1.0 \times 10^4$ to around $3.2 \times 10^5$ cells per square centimeter.

39. The method of claim 31, wherein said culture is maintained for up to 30 days.

40. The method of claim 31, further comprising the step of performing a bioassay in said culture vessel.

41. The method of claim 40, wherein said bioassay is enzyme based.

42. The method of claim 40, wherein said bioassay is fluorescence based.

43. A method for culturing neurons for high throughput analysis comprising the steps of:
   a. isolating neurons;
   b. maintaining neurons in the culture medium of claim 1;
   c. dissecting isolated neurons in the culture medium of claim 1 under conditions to obtain neuronal cells;
   d. filtering the neuronal cells;
   e. adding neuronal cells in an appropriate concentration to a culturing vessel;
   f. adding β-D-arabinofuranoside to the culture medium in an amount effective to inhibit the proliferation of non-neuronal cells;
   g. maintaining the neuronal cells in the culture medium of claim 1 in a carbon dioxide concentration between 3% and 10%;
   h. maintaining the neuronal cells in the culture medium of claim 1 in a humidity concentration around 100%; and
   i. maintaining the neuronal cells in the culture medium of claim 1 at a temperature of around 37° C.

44. The method of claim 43 wherein said culturing vessel comprises a tissue culture plate.

45. The method of claim 43 wherein said tissue culture plate is a 96-well plate.

46. The method of claim 43 wherein said tissue culture plate is a 384-well plate.

47. The method of claim 43 wherein said tissue culture plate is coated with poly L-lysine.

48. The method of claim 43 wherein said appropriate concentration of neuronal cells is from around $1.0 \times 10^4$ to around $3.2 \times 10^6$ cells per square centimeter.

49. The method of claim 43 wherein said appropriate concentration of neuronal cells is from around $1.0 \times 10^4$ to around $3.2 \times 10^5$ cells per square centimeter.

50. The method of claim 43, wherein said culture is maintained for up to 30 days.

51. The method of claim 43 wherein said tissue culture plate is coated with poly L-lysine.

52. The method of claim 43, further comprising the step of performing a bioassay in said culture vessel.

53. The method of claim 43, wherein said bioassay is enzyme based.

54. The method of claim 43, wherein said bioassay is fluorescence based.

55. A kit for culturing neurons for a bioassay, comprising:
   a. the medium of claim 1;
   b. at least one tissue culture vessel; and
   c. instructions to perform said bioassay.

56. The kit of claim 55, further comprising components of said bioassay.

* * * * *

UNITED STATES PATENT AND TRADEMARK OFFICE
CERTIFICATE OF CORRECTION

PATENT NO. : 6,506,576 B2
DATED : January 14, 2003
INVENTOR(S) : Belcher

It is certified that error appears in the above-identified patent and that said Letters Patent is hereby corrected as shown below:

<u>Title page,</u>
After "Inventor: Scott M. Belcher, 5824 Lee Ave., Little Rock, AR (US) 72205", insert -- [73] Assignee: Board of Trustees of the University of Arkansas, Little Rock, AR (US) --

Signed and Sealed this

Thirteenth Day of May, 2003

JAMES E. ROGAN
*Director of the United States Patent and Trademark Office*